United States Patent [19]
Rocci, Jr. et al.

[11] Patent Number: 5,676,129
[45] Date of Patent: Oct. 14, 1997

[54] DOSAGE COUNTER FOR METERED DOSE INHALER (MDI) SYSTEMS USING A MINIATURE PRESSURE SENSOR

[75] Inventors: Mario L. Rocci, Jr., Utica; Daniel J. Rossiter, Oneida; Robert K. Isensee, Blossvale; Michael L. Ferrara, New York Mills; Allen H. Salerno, Sherrill, all of N.Y.

[73] Assignee: Oneida Research Services, Inc., Whitesboro, N.Y.

[21] Appl. No.: 616,152

[22] Filed: Mar. 14, 1996

[51] Int. Cl.$^6$ ................................................. A61M 11/00
[52] U.S. Cl. ....................... 128/200.23; 128/200.14; 128/205.23
[58] Field of Search ................... 128/200.14, 200.23, 128/205.23, 204.23, 202.22, 203.14, 203.15, 203.24; 222/635, 649, 23

[56] References Cited

U.S. PATENT DOCUMENTS

| | | | |
|---|---|---|---|
| 5,020,527 | 6/1991 | Dessertine | 128/200.14 |
| 5,284,133 | 2/1994 | Burns et al. | 128/200.14 |
| 5,363,842 | 11/1994 | Mishelevich et al. | 128/200.14 |
| 5,373,851 | 12/1994 | Reinhold et al. | 128/716 |
| 5,392,768 | 2/1995 | Johansson et al. | 128/200.14 |
| 5,404,871 | 4/1995 | Goodman et al. | |
| 5,411,173 | 5/1995 | Weinstein | |
| 5,450,336 | 9/1995 | Rubsamen et al. | |
| 5,482,030 | 1/1996 | Klein | |
| 5,522,378 | 6/1996 | Riston et al. | 128/200.14 |

OTHER PUBLICATIONS

"Smart Device Actuates Metered Dose Inhaler At Best Time For Effective Drug Delivery" Spray Technology & Marketing for Mar. 1996, pp. 32–33.
Gerhard Levy, "Patient–Oriented Pharmaceutical Research: Focus on the Individual" Pharmaceutical Research, vol. 12, No. 7, 1995 pp. 943, 944.

*Primary Examiner*—Vincent Millin
*Assistant Examiner*—William J. Deane, Jr.
*Attorney, Agent, or Firm*—Sughrue, Mion, Zinn, Macpeak and Seas

[57] ABSTRACT

A method and apparatus for directly counting the number of doses expended from a Metered Dose Inhaler (MDI) medicinal delivery system. A miniature pressure sensor and microprocessor is used to detect the pressure pulse in the transfer channel of the mouthpiece of the MDI through which the inhaler dose (the prescribed mixture of aerosol propellant and medicinal drug) is released. The microprocessor processes data reflecting the dynamics of the pressure pulse and counts the number of doses administered. The microprocessor displays the counted doses (or doses remaining) on a miniature digital display. Additional information also may be provided to a user from the display or via an audible signal.

22 Claims, 6 Drawing Sheets

DOSAGE COUNTER FOR METERED DOSE INHALER (MDI) SYSTEMS USING A MINIATURE PRESSURE SENSOR

BACKGROUND OF THE INVENTION

A Metered Dose Inhaler (MDI) is a pharmaceutical delivery system that is commonly used to administer inhaled prescription drugs to treat a variety of conditions, including bronchospastic conditions such as asthma. MDI products contain aerosols which are generally solutions, primary emulsions, or suspensions of the active constituent along with propellant contained in a pressurized canister.

A conventional MDI consists of: 1) a canister, usually made of metal, approximately two inches high and one inch in diameter, 2) a metered dose valve and dispensing nozzle that is affixed to the top of the canister and is used to deliver a fixed quantity of the dose when the nozzle is depressed, 3) a plastic cap (the "mouthpiece") that is used to actuate the dispensing nozzle and to direct the dose into the patients lungs through the mouth; and 4) the contents of the canister, which usually consists of a mixture of an aerosol propellant and drug that is mixed or suspended in the propellant. The aerosol propellant acts as a carrier medium to deliver the drug. A propellant may be a single aerosol or a mixture of aerosols.

At room temperature, the aerosol propellant creates a saturated vapor pressure inside the canister. Upon actuation of the device, the internal pressure in the canister forces a metered quantity of liquid through the valve orifice and atomizes the actuated material. The pressure must be adequate to propel a metered quantity of the dose (propellant and medicinal drug) out of the canister each time the MDI is actuated, creating a plume or "puff". The expended dose passes out of the metering nozzle, through a small "transfer" channel in the plastic cap, and into a delivery channel that directs the dose into the patient's mouth. The patient inhales the administered dose while depressing and then releasing the cap (mouthpiece) of the MDI so as to actuate the metered dose delivery.

MDI products currently offer the benefits of bronchodilator, steroid, and other drug delivery with less systemic effects than would normally be observed following intravenous therapy. The MDI products also may be applied to the delivery of drugs such as Leukotriene antagonists as well as proteins and peptides.

The effective dose of drug delivered from a MDI product should be adequate and reproducible from actuation to actuation when treating a patient with asthma. For example, inappropriate and variable doses of bronchodilators during an acute asthmatic attack can have life-threatening consequences. Moreover, corticosteroids are often administered chronically to patients with asthma as a prophylactic measure and a high degree of dose-to-dose uniformity offers the greatest amount of protection. Two major determinants of the effective dose which a patient receives from a metered dose inhaler product are the dose delivered from the MDI, as well as the size of the particles inhaled into the pulmonary system.

Another consideration is that MDI pharmaceutical manufacturers typically label the packaging and/or the MDI with a "labeled dose", which is the maximum number of doses to be used. MDI products typically contain overfill to ensure good dose to dose reproducibility for the number of "labeled doses" of the product. For these reasons, it is essential that the device delivers an accurate and consistent dose from actuation to actuation from the first until the "labeled dose" is reached. It is also important that the particle size is maintained at a level acceptable to penetrate deeply into the pulmonary tree for maximum efficacy. The current manufacturing practice of overfilling MDI products permits actuation of the MDI well beyond the "labeled dose". When the "labeled dose" is exceeded, the dose strength could result in suboptimal therapy.

There are no easy, reliable ways currently available to the patient to determine when a canister's "labeled" contents have been consumed and that the patient has reached the "labeled dose". Typically patients will use metered dose inhaler products until the entire canister is exhausted. This could represent 25% or greater actuations beyond that labeled for this pharmaceutical product. Thus, a mechanism which would aid the patient in tracking the number of actuations which have been used for a given canister would aid the patient in determining when an MDI canister should be discarded and a new MDI canister used. The development of such a device would enhance the ability of a patient to comply or adhere to a prescribed dosing regimen. It is well appreciated that failure to adhere to medication dosage regimens can have a "profound influence on health care outcomes". (Levy; Pharm. Res. 12, No. 7: 943–944, 1995).

Any improvement in the treatment of asthma could result in reduced hospital stays and reductions in related health care costs. From a pharmacoeconomic standpoint, this would be highly desirable and third party insurers would likely provide reimbursement for the added cost of innovations which could reduce the cost of treating this disease in the hospital.

One approach to identifying each actuation of a MDI and to determining the number of actuations for a given canister is seen in U.S. Pat. No. 5,020,527 (Dessertine). However, the actuation of the MDI is identified by the mechanical operation of a lever each time the canister is depressed for delivery of a dose, and the number of actuations of the lever is counted. This approach is deficient because the requirement for a mechanical actuation of a switch presents the greater possibility of false actuations or failed actuations, thereby providing erroneous readings.

Accordingly, the invention is concerned with the solution of these and other problems presently encountered in the art.

SUMMARY OF THE INVENTION

The present invention involves the use of a pressure sensor to measure the pressure changes in the transfer channel of the mouthpiece of a Metered Dose Inhaler (MDI) medicinal delivery system. Pressure changes may result from one or both of the dispensing of a dose and the inhale process of a patient, or may also result from the effect of other events.

It is, therefore, the main object of the present invention to provide a method, and an apparatus associated therewith, by which the number of doses consumed in a MDI system are counted for the purpose of assisting patients in complying with prescribed use.

It is also the object of the present invention to provide a method of counting the number of doses consumed in a MDI medicinal delivery system using conventional technology that is readily available at low cost.

It is another object of the present invention to provide a method of counting the number of doses consumed in a MDI medicinal delivery system in a direct manner of measuring the pressure rise and fall (the pressure pulse) within the transfer channel of the mouthpiece of the MDI as a direct result of the transfer of a dose, thus measuring the physical event of dose transfer to the patient, and avoiding indirect methods such as mechanical counter approaches which do not actually verify that a dose was administered.

It is another object of the present invention to provide a method of counting the number of doses consumed in a MDI medicinal delivery system in a reliable manner by measuring the pressure pulse within the transfer channel of the mouthpiece of the MDI by using decision making software that can be programmed to prevent false dose counting.

It is another object of the present invention to develop low cost models that may be disposed of with each prescription and, also, to develop more elaborate models that would be more advanced in additional features and would be reusable.

It is another object of the present invention to embody other common capabilities of available low-cost microprocessors so that additional features may be added that will assist the patient in adhering to prescription requirements, including, but not limited to, standard capabilities of microprocessors to store data, to perform programmed logic, to measure time and to display messages or provide alarms. Features such as the display of the elapsed time since the last dose, or the display of messages such as "shake before using", or "Use ONLY 100 doses" could assist the patient in complying with the prescription requirements.

It is another object of the present invention to embody other common features of microprocessors that would be readily available with this invention by adding components to the microprocessor that will assist the patient in adhering to prescription requirements, including, but not limited to, common capabilities of microprocessors to activate add-on components such as a miniature speaker (to beep), or, to measure the output from a piezoelectric sensor or other motion sensing device to sense motion (as when the patient shakes the MDI, or does not shake the MDI, or does not shake the MDI long enough) so as to assist the patient in complying with the prescription requirements.

It is another object of the present invention to provide a method of counting the number of doses consumed in a MDI medicinal delivery system to embody the spirit and scope of sensing the pressure rise and fall (or pressure pulse) in the transfer channel to similar applications of MDI technology such as nasal dose applications, and even topical applications of medicines.

These and other objects are achieved by providing a mouthpiece for an MDI that uses a pressure sensor and by detecting changes of pressure that occur when a drug dose is properly delivered. The pressure sensor is positioned to detect the pressure in the transfer channel or the delivery channel of the mouthpiece of an MDI, and to identify the existence of pressure changes. The pressure sensor is connected to a microprocessor.

The microprocessor is programmed at least to determine the existence of a pressure pulse and to count the detected pressure pulses in the mouthpiece. An adequate threshold voltage for sensing the pressure pulse, over a determined period of time, is used so as to define conditions that would equate to a "Counted Dose". The algorithm used by the microprocessor is programmed to eliminate the occurrence of false counts and missing counts and thus make the recording of doses reliable. As would be understood by one of ordinary skill, such algorithms would depend on the MDI system design criteria and are therefore not fixed parameters for all MDI designs.

The microprocessor is further programmed to perform other desired functions as well, including the provision of messages and alarms via displays, speakers or buzzers and tactile warning devices. Programming for these functions would also be understood and readily implemented by one of ordinary skill in the art.

BRIEF DESCRIPTION OF DRAWINGS

The invention will be more easily understood with reference to the accompanying drawings, wherein.

DETAILED DESCRIPTION OF THE INVENTION

Figure 2:
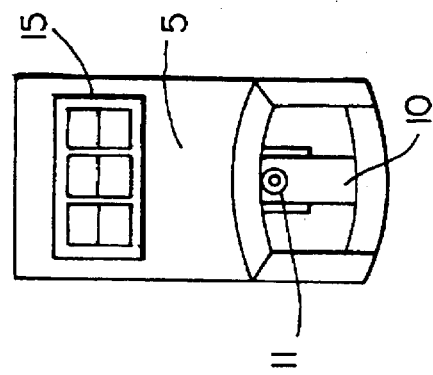
FIG. 2 is a front view of the mouthpiece showing an opening to the delivery channel and a display.
Figure 1:
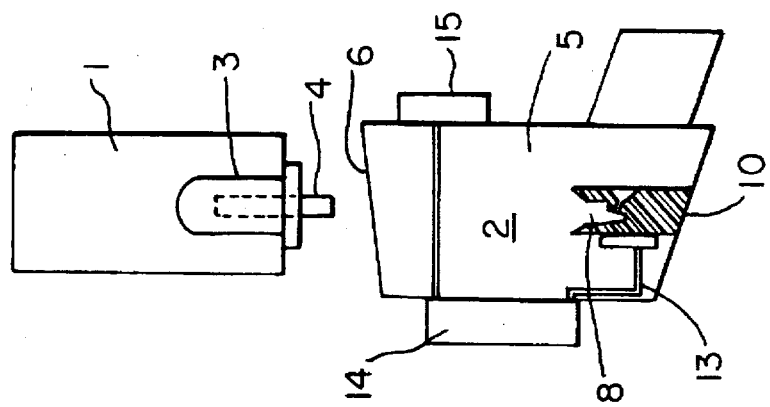
FIG. 1 is a schematic view showing an MDI canister with metered dose valve and dispensing nozzle and a mouthpiece that attaches to the canister.

A Metered Dose Inhaler (MDI) that embodies the present invention is seen in FIGS. 1 and 2 and has two pieces of apparatus, a canister 1 and a mouthpiece 2. The canister 1 is typically cylindrical, made of metal and has a metered dose valve 3 and dispensing nozzle 4 affixed to the top of the canister. The mouthpiece 2, usually made of plastic, is manually mated to the nozzle end of the canister by the patient. The mouthpiece 2 comprises a body 5 that is formed with a cylindrical channel 6 for receiving and firmly holding the canister 1 in an operational position, wherein the nozzle 4 is adjacent a transfer channel 7 formed within the mouthpiece. Preferably, the canister 1, cylindrical channel 6, nozzle 4 and transfer channel 7 are coaxial and are sized to provide an adequate sealing relationship between the nozzle-end of the canister and the transfer channel 7 so that upon operation of the valve 4, the dose of medicine will not escape at the interface between the canister and mouthpiece.

Figure 3:
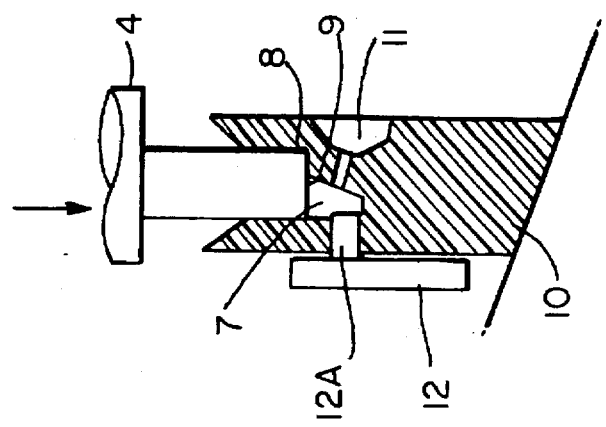
FIG. 3 is an expanded view of the transfer channel showing a pressure sensing device in operative engagement with the transfer channel of a mouthpiece.

The MDI dose delivery is actuated by a patient manually squeezing the mouthpiece 2 and canister 1 together. A mating structure 8 of the mouthpiece 2 engages the nozzle 4 of the canister, causing it to be depressed as a result of the squeezing force, thereby actuating the metered dose valve. With reference to FIG. 3, the metered dose volume is forced through the valve orifice 9, then through the transfer channel 7 that is formed within the channel body 10 of the mouthpiece 2. The dose volume will exit the transfer channel and enter a delivery channel 11, through which it is directed toward the patient. The dose is forced out of the metered valve 3, not by a "mechanical pump", but due to the pressure developed from the saturated vapor pressure created by the propellant.

As the dose (a mixture of propellant and medicinal drug) is released from the pressurized canister, the propellant quickly volatilizes and expands within the transfer channel 7, causing a pressure burst that propels the dose out through the transfer channel exit and into the delivery channel 11. This pressure rise and fall in the transfer channel 7 is sensed by a pressure sensor 12 that is mounted to the body 10 and has its sensing structure 12A in direct contact with the transfer channel 7.

In the embodiment of FIG. 1 that demonstrates the concept of dose counting, a miniature solid state (silicon) pressure sensor is affixed to the wall of body 10 with its sensing structure implanted into a hole formed in the body and the tip of the sensing structure flush to the inside wall of the transfer channel 7 of the mouthpiece 2 of an MDI device. The pressure sensor 12 may be a Model NPC-109, manufactured by Lucas NovaSensor. The sensor is housed in a polycarbonate gel tube and covered with a dielectric gel (e.g., silicone) in order to protect the sensor from harsh environments, reduce additional volume in the transfer passage and provide a medically acceptable media interface. Pressure sensors are available to measure different pressure ranges, the dynamic pressure range of the sensor in the preferred embodiment being −0.58 psi to +5.8 psi, with a sensor response time of 0.8 millisecond. The sensor is electronically connected by a connector 13 to circuitry, as shown in FIG. 4, that includes a microprocessor 14, a Liquid Crystal Display (LCD) 15, and an operational amplifier 16.

Figure 4:
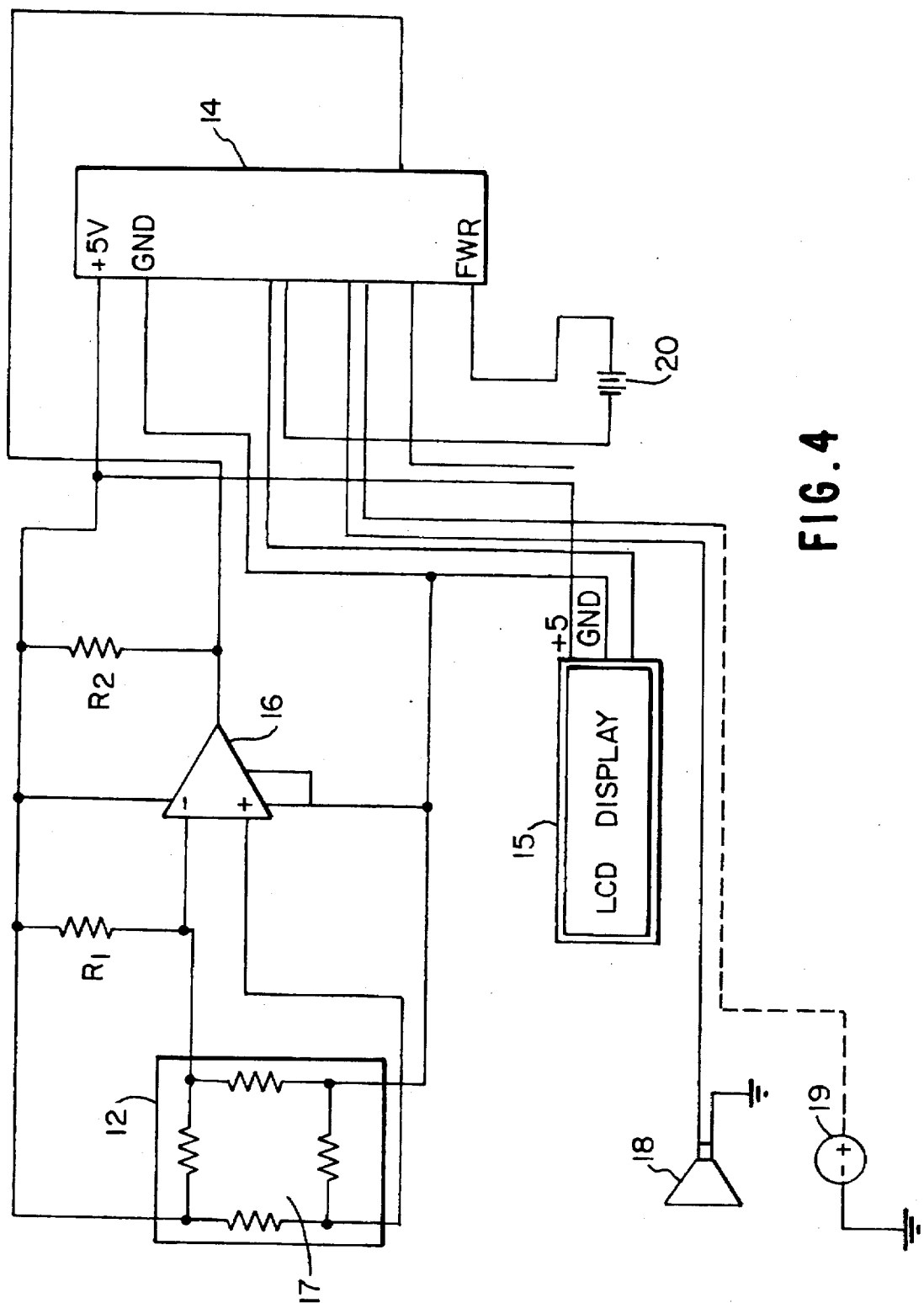
FIG. 4 is a circuit diagram for a simplified pressure threshold level sensor design that is applicable to the basic method of counting doses.

As seen in FIG. 4, the pressure sensor 12 may be a silicon device of conventional technology which reacts to differential pressure, and functionally acts as a Wheatstone Bridge 17 (a network of precision resistors). When a DC voltage is applied across the network inputs (+Vin and −Vin) and pressure differential is zero, resistors are in balance resulting in a zero voltage difference between the + and − outputs of the bridge. When the resistance of one of the resistors is changed due to change in pressure in the transfer channel, the voltage will deflect in a positive or negative manner reflecting the change.

The outputs of the pressure sensor 12 are applied across the +/− inputs of the operational amplifier 16, along with external pull-up resistor R2 and bias resistor R1 act as a voltage comparator. The values of these resistors are chosen to provide a threshold voltage, (e.g., 35 millivolts). Any voltage output from the pressure sensor that is above the threshold value would set the output of the operational amplifier to the "ON state" so as to be "sensed" or "counted" by the microprocessor. Any voltage output from the pressure sensor below the threshold value would set the output of the operational amplifier to the "OFF state" so as to be "Not sensed" or "Not counted" by the microprocessor. Any "Not sensed" output from the pressure sensor would drive the output of the operational amplifier 16 to its minimum value (e.g., 0 Volt).

The operational amplifier 16 converts the very small voltage increase from the pressure sensor (e.g., approximately 25 to 65 millivolts) to a larger voltage (e.g., about 5 Volts) output needed to trigger the threshold (e.g., about 1.4 Volt) for the hi/lo logic input of the microprocessor 14. The actual voltage output might vary depending on the source voltage provided (i.e. 3 volts instead of 5 volts).

The microprocessor 14 may be programmed to display the "Remaining Doses" and the "Elapsed Time" from the last dose. The Remaining Doses may be pre-set to 120. The microprocessor 14 would then "Read" the "On" (5 volt) or "Off" (0 volt) state of the operational amplifier 16. If the "Off state" is detected, the microprocessor 14 is programmed to increment an elapsed time counter, redisplay the elapsed time, then re-read the state of the operational amplifier 16. If the microprocessor detects an "On state", the microprocessor is programmed to decrement the remaining dose count by one, redisplay the "remaining dose", increment the elapsed time counter, redisplay the elapsed time, then wait a predetermined "delay time" period before sensing the state of the operational amplifier again. Preferably, a delay time interval (e.g., 0.75 seconds) is provided to reliably detect a pressure pulse as a dose count. An insufficient delay time may result in occasional double counting because the pulse had not completely been dissipated through the transfer channel. Excessively longer delay time intervals could result in missed dose counts because the patient would be able to manually trigger two puffs within the period, even though such quick consecutive dose administrations would not be recommended by the manufacturer. Tests conducted using a 0.75 second delay time interval produced 100% accuracy in counting when 360 doses were administered every 5 seconds. No false dose counts were detected when the device was left idle for over 5 days.

In a further enhancement of the first embodiment of the invention, a beeping device may be added to the electronic unit of FIG. 4. In this regard, a miniature speaker device 18 may be connected to one of several available microprocessor outputs and the microprocessor may be prepared to turn the beeper ON or OFF based on the elapsed time or remaining dose counter status. Thus the patient could be audibly warned when to take the next dose and/or when the "labeled dose" was imminent.

Finally, the circuit uses a battery 20 as a power supply, the battery being small enough to be carried by the mouthpiece 2, together with the microprocessor 14 and pressure sensor 12.

Figure 5:
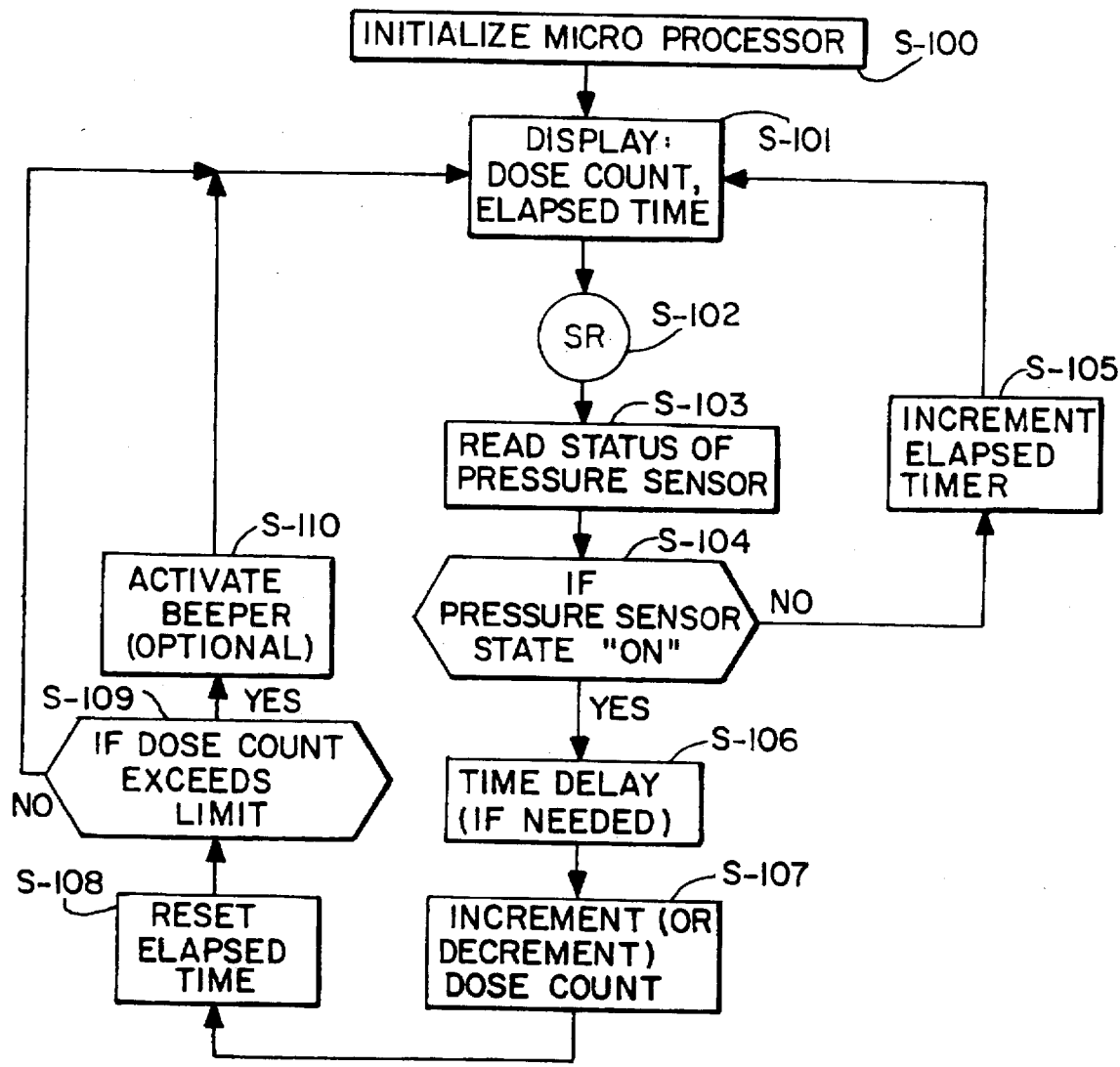
FIG. 5 is flowchart evidencing the logic of a simple dose counter seen in FIG. 4.

FIG. 5 illustrates a flowchart for the simple dose counting operation of the circuit illustrated in FIG. 4. The microprocessor is initialized at S-100. The dose counter could be either incremented to display the doses used or decremented to display the doses remaining. In this example, the display of "Remaining Dose" is used; thus, a dose counter in the microprocessor is set to 120 and the dose counter is decremented each time that a dose is detected. The elapsed time since the last dose is set to zero. A delay time parameter is set to 750 milliseconds and the dose count limit is preset to 5 to allow a warning beep when the remaining doses is 5 or less.

In step S-101, the microprocessor displays the current remaining dose and the current elapsed time. Step S-102 concerns the subroutine (SR) processing related to an optional motion sensor application, as subsequently discussed with respect to FIG. 8. The pressure sensor is then read at step S-103, indicating a value of ON or OFF, based on the circuit design of FIG. 4. The OFF state represents the state where there is very little pressure differential above atmospheric pressure (approximately 10% of the peak pulse pressure). The ON state represents a state where the pressure differential is above atmospheric pressure (greater than approximately 10% of the peak pulse pressure). The threshold should be high enough so that it cannot be activated by the patient blowing into the mouthpiece. If the state is ON (S-104), the program may wait for a predetermined time at step S-106 to allow the pressure to dissipate. The dose counter is then decremented by one at step S-107 and the elapsed timer is reset to zero (S-108). If the dose count is less than the dose count limit (S-109), a beep is activated for a fraction of a second (S-110). The new dose count and elapsed time is then redisplayed. If the state is OFF (S-104), the program increments the elapsed timer (S-105) and redisplays the dose counter and elapsed time.

Alternative embodiments may be provided by adding an advanced pressuring sensing capability, by 1) selecting a pressure sensor device with optimal dynamic pressure range for the designed MDI, and 2) using linear circuitry techniques to enable the microprocessor to evaluate the pressure pulse in fine detail, as if to model the pressure pulse shape. The microprocessor could be programmed to compare the measured pressure pulse and compare it to a predetermined "desired pulse". Deviations between the measured pressure pulse and desired pressure pulse would determine abnormalities of dose administration, such as 1) a partially clogged dispensing path, 2) a leaking canister, 3) inadequate metering of the dose by the Metering Valve, 4) an abnormal squeezing procedure by the patient. Such adaptations are available with current pressure sensor technology and current circuit technology.

Figure 6:
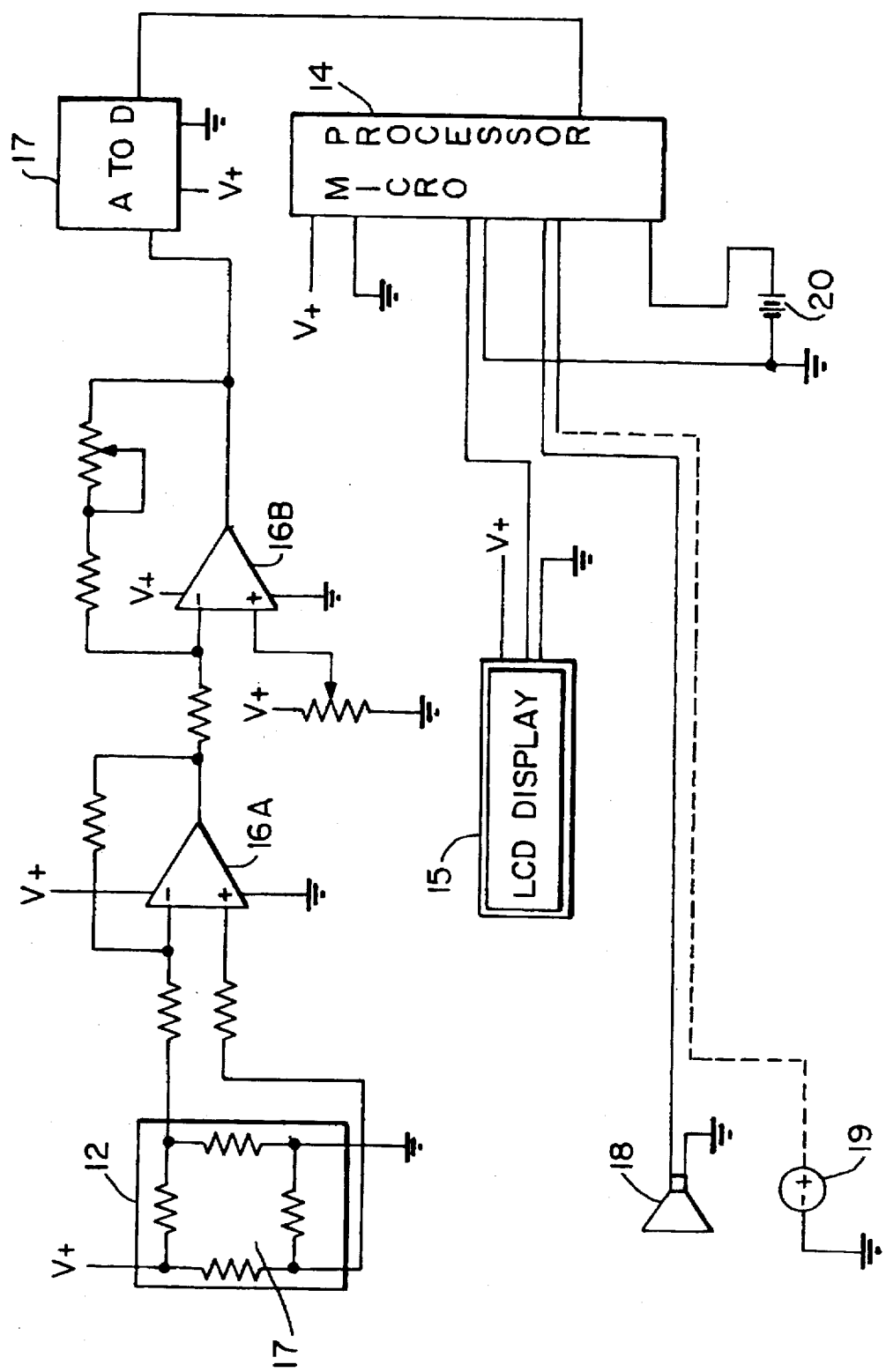
FIG. 6 is a circuit diagram for a more complex design that can achieve an evaluation of the pressure pulse based on pressure and time data.

The circuit of FIG. 6 includes the arrangement of pressure sensor 12, microprocessor 14, display 15, buzzer 18, motion sensor 19 and battery as seen in FIG. 4. However, the output of pressure sensor 12 is provided to a linear amplifier 16A, 16B with analog-to-digital converter 17 to send the digital amplitude measurements to the microprocessor 14. The microprocessor fills a data buffer-stack with the pressure pulse stream in the order that measurements are received. Each new pressure measurement is added to the top of the buffer stack and the oldest data point at the bottom of the stack is lost. The data in the stack at any point in time is used to evaluate the state of a dose pressure pulse to determine if a dose has been administered and to determine if the dose pulse was within designed limits. Knowledge about the desired pressure pulse profile must be preprogrammed into the memory and predictable faults in MDI operation must be pre-programmed as algorithms. These features would be implementable by the programmer having ordinary skill in the art.

Figure 7:
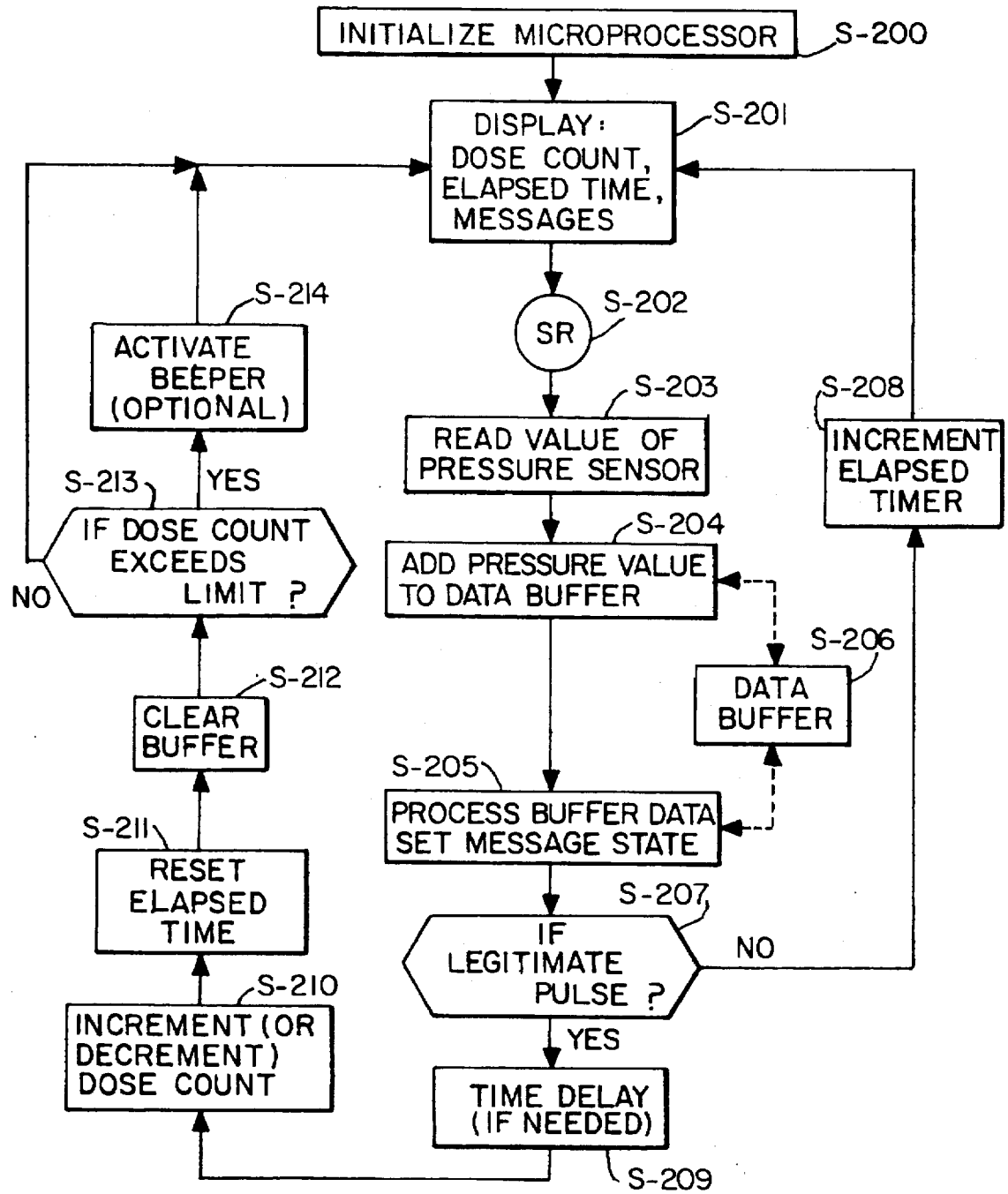
FIG. 7 is a flowchart for a dose counter as seen in FIG. 6.

The circuit of FIG. 6 can be operated according to the flow chart of FIG. 7. Specifically, in this approach, the value of the pressure vs. time is measured so as to create a profile of the pressure pulse shape which would be used to make more advanced decisions about dose counting and to evaluate the quality of the dose profile and compare it to a desired (ideal) dose profile. The microprocessor is initialized in S-200. The dose counter could be either incremented to display the doses used, or decremented to display the doses remaining. In this example, the display of the "Remaining Dose" is preferred so the dose counter would be set to 120 (for example) and the dose counter would be decremented each time a dose was detected. The elapsed time (since the last dose) would be set to zero. The delay time referenced in S-209 would be set, if needed. The dose count limit in S-213 would be preset to 5 to allow a warning beep when the remaining doses was 5 or less. An array of short messages would be pre-programmed into the memory. The current message value would be pre-set to 0 (no message).

In S-201, the microprocessor would be programmed to display the current remaining dose, the elapsed time and the current message. S-202 is an optional motion sensor application (SR) discussed in FIG. 8. Step S-203 would be programmed to read the value of the pressure sensor which would be converted to a digital value by the A to D converter 17. The digital pressure value would then be added to the stack buffer (S-204 and S-206). The data in the Stack buffer (S-206) would then be compared (S-205) to an ideal pressure pulse and also to predictable fault pulses to make logical decisions about the pressure pulse. Numerous comparison techniques could be employed. A simple difference between the measured pulse profile and ideal pulse profile would indicate a "legitimate dose" pressure pulse when the difference was approximately zero. A "clogged orifice" in the mouthpiece transfer channel would be indicated if the pulse width exceeded the ideal pulse width by approximately 50%. An "almost empty" canister would be indicated by a peak pressure value of less than approximately 75% of the ideal pulse peak value. A "leaking" canister would be indicated by an approximately constant, slightly elevated pressure level in the mouthpiece transfer channel. This threshold should be high enough so that it can not be activated by the patient blowing into the mouthpiece. If the pressure pulse is not a legitimate pulse (S-207) then either a fault pulse would be possible or, the most common situation, no pulse would exist. If it is a fault pulse, then the message would change to indicate the fault. If it were a fault pulse or no pulse, the elapsed time would be incremented (S-208) and the new dose count, elapsed time, and messages would be redisplayed. If the pulse were a legitimate pulse, the program would wait a pre-defined time delay (S-209) in order to allow the pressure pulse to completely dissipate (this delay is optional and may not be needed). The dose counter would decremented by 1 (S-210) and the elapsed timer would reset to zero (S-211). All data in the stack buffer would be cleared (S-212). If the dose count was less than the dose count limit, the beep would be activated for a fraction of a second (S-214). The new dose count, elapsed time, and messages are then redisplayed.

A further feature of the first and second embodiments is the addition of a motion sensor 19, which may detect the shaking motion of the MDI, where it is required to shake the contents a predetermined amount prior to use. The signal generated by the motion sensor may be input to the microprocessor 14 for detection and processing, and for the activation of a display or audible signal to signify that the proper amount of shaking has been provided.

Figure 8:
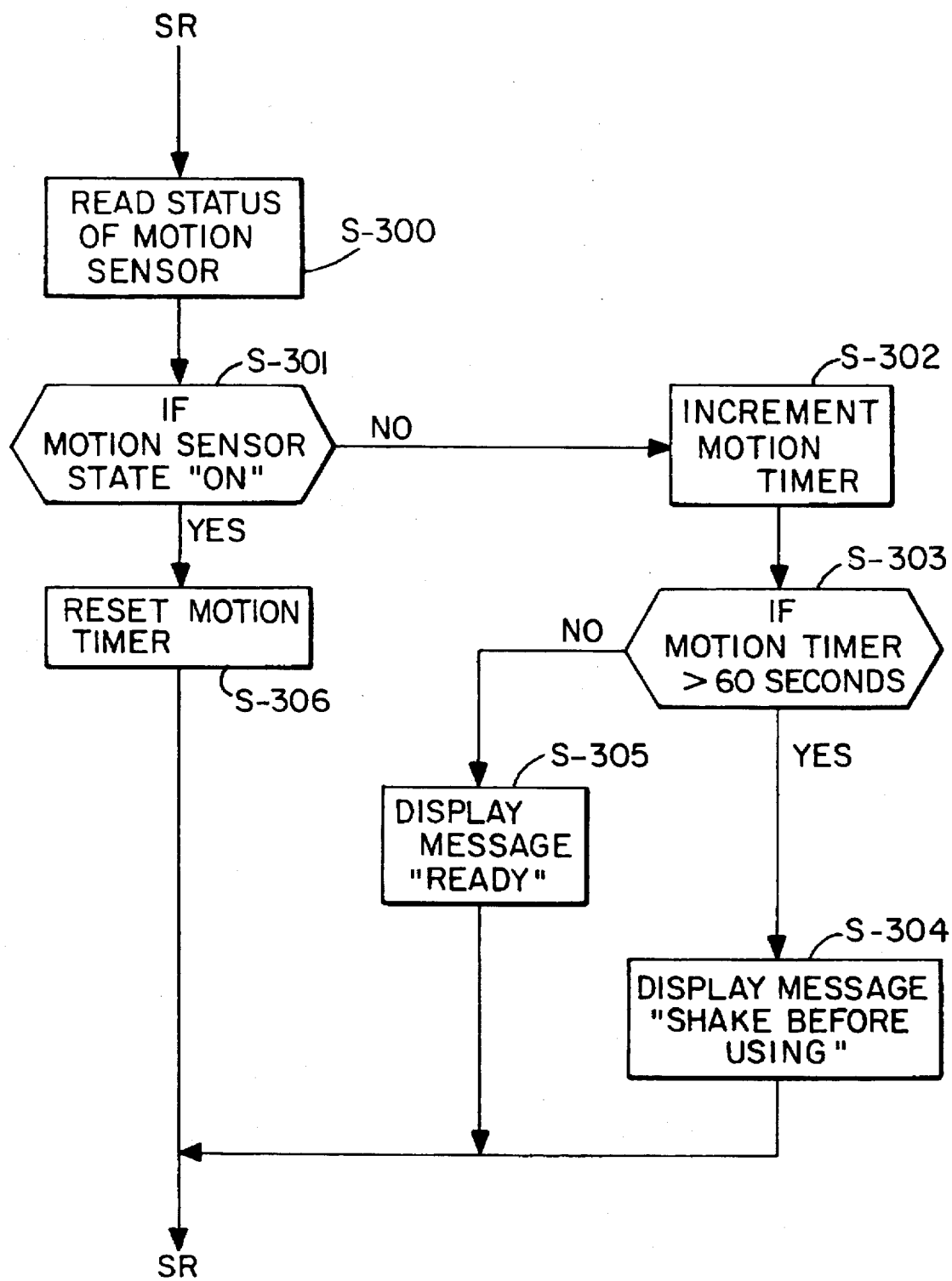
FIG. 8 is a flowchart representing the logic applicable to the use of a motion sensor to determine if a canister has been shaken before use.

The operation of the microprocessor using the miniature motion sensor is seen in the flowchart of FIG. 8 where the motion sensor is read (S-300) to determine (S-301) if the sensor is in motion, i.e., beyond a threshold of time and/or magnitude. The threshold is programmed so as to avoid detection of ordinary handling, but would detect shaking of an adequate amount and/or for an adequate period of time. If the minimum amount of motion (time/magnitude) was detected, the motion timer would be reset to zero (S-306) and the process would proceed as in FIGS. 5 and 7 and continue to cycle through the steps as appropriate. If motion were not detected, the motion timer would increment its current count (S-302). If the motion timer is less than a predetermined period of time, the minimum amount of shaking would have been provided and the message would be "ready" (S-305). If the motion timer is greater than a predetermined time, e.g., 60 seconds, the canister would have been at rest for a period sufficient to have the contents separate and a minimum amount of shaking would again have to be provided, thus the message would be "shake before using".

When implementing the dosage counter, the MDI should not be designed to lock when it reached the labeled number of actuations. Rather, it should beep and/or display a warning message during the last five or other selected number of actuations since locking of the dosage form may cause a problem during an acute asthmatic attack. During such an attack, bronchodilators administered in less than labeled doses would be of some relative benefit compared to no dose being available at all. Further advanced evolution of the invention could permit an assessment of the patient's pulmonary status following delivery of the drug. The invention could also contain different auditory warnings, for example, indicating whether or not the patient inspired forcefully enough.

MDI technology also can be used to administer doses to the nasal passages and it is to be understood that nasal dose applications are in the spirit and scope of this invention. In fact, even topical applications using a pressure delivery system can be monitored and relevant information displayed.

While the present invention has been illustrated and described with respect to preferred embodiments, it is not intended to be thereby limited. It would be understood by one of ordinary skill in the art that various omissions; modifications, substitutions and changes can be made with respect to the details of any device that implements the invention, without departing from the spirit of the present invention, as set forth in the appended claims.

We claim:

1. A drug dispensing apparatus comprising:
    a pressurized container for a dispensable drug, said container comprising at a delivery end a metered dose valve and a nozzle, said nozzle at its exit providing a metered dose at a predetermined pressure when said metered dose valve is actuated;
    a delivery apparatus comprising a transfer passage and a delivery passage, said transfer passage being in communication with said nozzle exit for receiving a metered dose of said drug substantially at said predetermined pressure, and a pressure sensor for detecting the changes in pressure in said transfer passage.

2. The drug dispensing apparatus as set forth in claim 1 further comprising means responsive to said pressure sensor for providing information concerning said drug delivery process.

3. The drug dispensing apparatus as set forth in claim 2 wherein said responsive means comprises a microprocessor in communication with said pressure sensor and a display.

4. The drug dispensing apparatus as set forth in claim 2 wherein said responsive means comprises a microprocessor in communication with said pressure sensor and an audible announcer apparatus.

5. The drug dispensing apparatus as set forth in claim 2 wherein said responsive means comprises a microprocessor in communication with said pressure sensor, said microprocessor being operative to count the number of times the pressure exceeds a predetermined threshold level.

6. The drug dispensing apparatus as set forth in claim 2 wherein said responsive means comprises a microprocessor in communication with said pressure sensor, said microprocessor being responsive to at least one of the duration and magnitude of pressure detected by said pressure sensor for determining the existence of pressure pulses.

7. The drug dispensing apparatus as set forth in claim 6 wherein said microprocessor counts down from a predetermined number.

8. The drug dispensing apparatus as set forth in claim 6 wherein said responsive means is operative to provide information at least at a predetermined count.

9. The drug dispensing apparatus as set forth in claim 1 wherein said delivery apparatus comprises a mouthpiece having a cylinder engagement chamber for sealingly receiving said delivery end of said container.

10. The drug dispensing apparatus as set forth in claim 1 wherein said container comprises a cylindrical canister having an outer circumferential dimension at said delivery end, and said delivery apparatus comprises a cylindrical channel for sealingly receiving said canister delivery end.

11. The drug dispensing apparatus as set forth in claim 1 further comprising a motion detector for detecting a shaking applied to said apparatus and means responsive to said motion detector for determining whether said shaking action satisfies predetermined criteria.

12. A delivery apparatus for use with a pressurized container having a metered dose valve and a nozzle for emitting metered doses of a drug, said nozzle at its exit providing a metered dose at a predetermined pressure when said metered dose valve is actuated, said apparatus comprising:
    a body comprising a structure for interfacing with said pressurized container;
    a transfer passage for communication with said nozzle exit for receiving a metered doses of said drug substantially at said predetermined pressure;
    a pressure sensor for detecting the changes in pressure in said transfer passage; and
    a delivery passage in communication with said transfer passage for providing said metered dose of said drug to a patient.

13. The drug dispensing apparatus as set forth in claim 12 further comprising a display and means responsive to an output of said pressure sensor for indicating a metered dose condition by said display.

14. The drug dispensing apparatus as set forth in claim 12 further comprising an audible announcer and means responsive to an output of said pressure sensor for indicating a metered dose condition by said announcer.

15. A method of monitoring the delivery of a metered dose from a pressurized container via a mouthpiece having a transfer passage for directing said metered doses from the container to the patient comprising:
    detecting dosage-related pressure increases in said transfer passage;
    counting doses on the basis of the number of times that said pressure increases are detected; and
    providing information in response to said counting step.

16. The method of monitoring as set forth in claim 15 further comprising detecting motion of said container and providing information in response to said motion detecting step.

17. The method of monitoring as set forth in claim 15 wherein said counting step comprises counting down from a predetermined number.

18. The method as set forth in claim 15 wherein said step of providing information comprises generating a visual message display.

19. The method as set forth in claim 15 wherein said step of providing information comprises generating an audible message.

20. The method as set forth in claim 15 further comprising the step of detecting a minimum amount of shaking and said providing information step further comprises providing information concerning said shaking step.

21. The drug dispensing apparatus of claim 1 wherein said pressure sensor has a sensing portion disposed for directly sensing pressure changes in said transfer passage.

22. The delivery apparatus of claim 12 wherein said pressure sensor has a sensing portion disposed for directly sensing pressure changes in said transfer passage.

* * * * *